United States Patent
Juraszyk et al.

[11] Patent Number: 5,614,531
[45] Date of Patent: Mar. 25, 1997

[54] ADHESION RECEPTOR ANTAGONISTS

[75] Inventors: Horst Juraszyk, Seeheim; Joachim Gante; Hanns Wurziger, both of Darmstadt; Sabine Bernotat-Danielowski, Bad Nauheim; Guido Melzer, Hofheim/Ts., all of Germany

[73] Assignee: Merck Patent Gesellschaft Mit Beschrankter Haftung, Germany

[21] Appl. No.: 390,669

[22] Filed: Feb. 17, 1995

[30] Foreign Application Priority Data

Feb. 19, 1994 [DE] Germany .......................... 44 05 378.9

[51] Int. Cl.⁶ .......................... A61K 31/44; C07D 471/04
[52] U.S. Cl. .......................................... 514/300; 546/121
[58] Field of Search .............................. 514/300; 546/121

[56] References Cited

U.S. PATENT DOCUMENTS

| | | | |
|---|---|---|---|
| 4,767,755 | 8/1988 | George et al. | 514/212 |
| 4,808,594 | 2/1989 | George et al. | 514/212 |
| 4,891,371 | 1/1990 | George et al. | 514/212 |
| 4,990,506 | 2/1991 | George et al. | 514/212 |
| 5,084,466 | 1/1992 | Alig et al. | 514/353 |
| 5,256,812 | 10/1993 | Alig et al. | 560/35 |
| 5,399,585 | 3/1995 | Alig et al. | 514/438 |
| 5,434,150 | 7/1995 | Austel | 514/228.5 |

FOREIGN PATENT DOCUMENTS

| | | |
|---|---|---|
| 234970 | 9/1987 | European Pat. Off. . |
| 261912 | 3/1988 | European Pat. Off. . |
| 267111 | 5/1988 | European Pat. Off. . |
| 381033 | 1/1990 | European Pat. Off. . |
| 459256 | 5/1991 | European Pat. Off. . |
| 462960 | 12/1991 | European Pat. Off. . |
| 512831 | 11/1992 | European Pat. Off. . |
| 512829 | 11/1992 | European Pat. Off. . |
| 540334 | 5/1993 | European Pat. Off. . |
| 4327027 | 8/1994 | Germany . |
| 93/19066 | 9/1993 | WIPO . |
| 94/18198 | 8/1994 | WIPO . |

OTHER PUBLICATIONS

Ruoslaliti E, Pierschbachen MD (1987) Science 238, 491.

*Primary Examiner*—C. Warren Ivy
*Assistant Examiner*—Evelyn Huang
*Attorney, Agent, or Firm*—Millen, White, Zelano, & Branigan, P.C.

[57] ABSTRACT

Compounds of the formula I

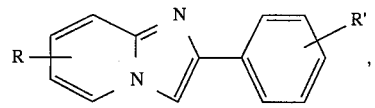

and the corresponding 5,6,7,8-tetrahydroimidazo[1,2-a]pyridine derivatives, their physiologically acceptable salts and/or solvates, inhibit the binding of fibrinogen to the corresponding receptor and can be used for the treatment of thromboses, osteoporosis, oncoses, stroke, myocardial infarct, inflammations, arteriosclerosis and osteolytic disorders.

8 Claims, No Drawings

ADHESION RECEPTOR ANTAGONISTS

The invention relates to compounds of the formula I

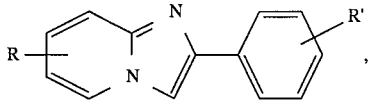

and to the corresponding 5,6,7,8-tetrahydroimidazo-[1,2-a]pyridine derivatives,
in which
R is Q or COX,
R' is Q when R is COX, and COX when R is Q,
Q is $NO_2$, $NH_2$, CN, $CSNH_2$, C(=NH)S-A, C(=NH)NHOH, C(=NH)—$NH_2$, $CH_2$—$NH_2$, $CH_2NH$—C(=NH)—$NH_2$, NH—C(=NH)—$NH_2$, $CH_2NHCO$—alk—$NH_2$, $CH_2NHCO$—Ar—C(=NH)$NH_2$, $CH_2NHCO$—Ar—$CH_2$—$NH_2$ or D,

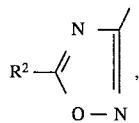

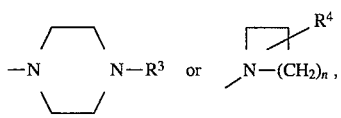

AA or AA' are each, independently of one another, an amino acid residue selected from the group consisting of Ala, β-Ala, Arg, Asn, Asp, Gln, Glu, Gly, Leu, Lys, Orn, Phe, Pro, Sar, Ser, Thr, Tyr, Val, C-allyl-Gly, C-propargyl-Gly, N-benzyl-Gly, N-phenethyl-Gly, N-benzyl-β-Ala, N-methyl-β-Ala and N-phenethyl-β-Ala,
$R^2$ is OH, A or Ar,
$R^3$ is —$(CH_2)_m$—$COOR^5$,
$R^4$ is —$(CH_2)_p$—$COOR^5$ or —$(CH_2)_q$—O—$(CH_2)_r$—$COOR^5$,
$R^5$ is H or A,
m is 1, 2 or 3,
n is 1, 2, 3 or 4,
p is 0, 1 or 2,
q is 0 or 1,
r is 1 or 2,
A is alkyl with 1 to 6 C atoms,
—alk— is alkylene with 1 to 6 C atoms
—Ar— is phenylene, and
Ar— is phenyl,
where any free amino or carboxyl groups can also be provided with protective groups known per se, and the physiologically acceptable salts and/or solvates thereof.

Compounds with a similar profile of action but having a different basic structure are disclosed in EP-A 10 381 033.

The invention was based at least with an object of finding novel compounds with valuable properties, in particular those which can be used to produce pharmaceuticals.

Upon further study of the specification and appended claims, further objects and advantages of this invention will become apparent to those skilled in the art.

These objects are achieved by the invention. It has been found that the compounds of the formula I and their solvates and salts have valuable pharmacological properties while being well tolerated. In particular, they inhibit the binding of fibrinogen, fibronectin and von Willebrand factor to the fibrinogen receptor of blood platelets (glycoprotein llb/lIla) as well as the binding thereof and other adhesive proteins such as vitronectin, collagen and laminin to the corresponding receptors on the surface of various cell types. The compounds thus exert an influence on cell-cell and cell-matrix interactions. They prevent, in particular, the development of blood platelet thrombi and can therefore be used for treating thromboses, stroke, myocardial infarct, inflammations and arteriosclerosis. The compounds furthermore have an affect on tumor cells by inhibiting metastasis thereof. They can thus also be used as antitumor agents.

There is evidence that tumor cells spreading from a solid tumor into the vasculature are carried by microthrombi and thus are protected from being detected by cells of the immune system. The second step of attachment to the vessel wall seems to be facilitated by microthrombi as well. Since the formation of thrombi is mediated by fibrinogen binding to the fibrinogen receptor (glycoprotein llb/lIla) on activated platelets, fibrinogen-binding inhibitors are expected to be effective as antimetastatics.

Also, since fibrinogen-binding inhibitors are ligands with fibrinogen receptor on platelets, they can be used as diagnostic tools for detection and localization of thrombi in the vascular in vivo. Thus, for example, in accordance with known procedures, the fibrinogen-binding inhibitors can be labeled with a signal generating or detectable moiety whereby, once the labeled fibrinogen-binding inhibitor is bound to a fibrinogen receptor on platelets, it is possible to detect and locate thrombi.

Fibrinogen-binding inhibitors are also very effective as research tools for studying the metabolism of platelets in the different activation states or intracellular signalling mechanisms of the fibrinogen receptor. For example, as described above, fibrinogen-binding inhibitors can be labeled with a signal generating or detectable moiety. The fibrinogen-binding inhibitor-signal generating/detectable moiety conjugate can then be employed in vitro as a research tool. By binding the conjugate to fibrinogen receptors, it is possible to monitor and study the metabolism of platelets, as well as the activation states and signalling mechanisms of the fibrinogen receptors.

The compounds are furthermore suitable for the prophylaxis and treatment of osteolytic disorders, in particular of osteoporosis, angiogenesis and restenosis after angioplasty.

The compounds additionally show an antimicrobial action and can be used in association with all treatments and interventions where microbial attack must be prevented. For example, by topical application in surgical procedures.

Suitable preparations for using the compounds as antimicrobial agents are, for example, injection vials, ampoules, solutions, and capsules. Carriers, excipients, and further additives are mentioned in Examples A–H. The amount of the inventive compound in the antimicrobial agents is preferably about 0.05–500 mg per dosage unit.

The properties of the compounds can be demonstrated by methods described in EP-A 10 462 960. The inhibition of fibrinogen binding to the fibrinogen receptor can be demonstrated by the method indicated in EP-A1 0 381 033. The platelet aggregation-inhibitingaction can be demonstrated in vitro by the method of Born (Nature 4832, 927–929, 1962). The inhibition of the interactions of $β_3$-integrin receptors with suitable ligands can be demonstrated by the method of J.W. Smith et al., J. Biol. Chem. 265, 12267–12271 (1990).

The invention furthermore relates to a process for preparing a compound of the above-mentioned formula I and of salts thereof, characterized in that
(a) a compound of the formula I is liberated from one of its functional derivatives by treatment with a solvolyzing or hydrogenolyzing agent, or in that (b) a compound of the formula II

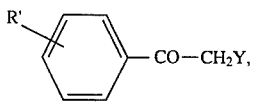

in which
R' has the stated meaning, and
y is Cl, Br, I, OH or a reactive esterified OH group or a leaving group which can easily undergo nucleophilic substitution,
is reacted with a pyridine derivative of the formula III

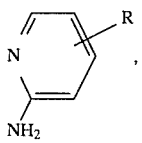

in which R has the stated meaning, or in that p0 (c) a radical R and/or R' is converted into another radical R and/or R' by
hydrolyzing an ester of the formula I or
subjecting a carboxylic acid of the formula I to esterification, conversion into an amide or linkage with an amino acid or a dipeptide under the conditions of peptide synthesis, or
catalytically hydrogenating an $NO_2$ and/or CN group or
converting a cyano group by addition of ammonia into a C(=NH)—$NH_2$ group or
converting a cyano group into a thiocarbamoyl group or
converting a thiocarbamoyl group into a methylsulfimido group or
converting a methylsulfimido group into an amidino group,
converting a cyano group by addition of $NH_2OH$ into a C(=NH)—NHOH group or
converting a C(=NH)—NHOH group into an amidino group,
converting a $CH_2NH_2$ group into an alkanoylaminomethyl group or
converting a 1,2,4-oxadiazole or 1,2,4-oxadiazolinone group into an amidino group, and/or in that
(d) a compound of the formula I is converted by treatment with an acid or a base into one of its salts.

The abbreviations of amino acid residues mentioned hereinbefore and hereinafter represent the residues of the following amino acids:
Ala alanine
β-Ala Pβ-alanine
Arg arginine
Asn asparagine
Asp aspartic acid
Asp (O But) β-butyl aspartate
Gln glutamine
Glu glutamic acid
Gly glycine
Leu leucine
Lys lysine
Orn ornithine
Phe phenylalanine
Pro proline
Sar sarcosine (N-methylglycine)
Ser serine
Thr threonine
Tyr tyrosine
Val valine.

Further meanings are given below:
BOC tert-butoxycarbonyl
CBZ benzyloxycarbonyl
DCCI dicyclohexylcarbodiimide
DMF dimethylformamide
EDCI N-ethyl-N'-(3-dimethylaminopropyl)carbodiimide hydrochloride
Et ethyl
Me methyl
OMe methyl ester
OEt ethyl ester
TFA trifluoroacetic acid.

The radicals R and R' have hereinbefore and hereinafter the meaning indicated for formula I. When a compound of the formula I has a chiral center, it can occur in several enantiomeric forms. All these forms and mixtures thereof, especially racemates, are included in the invention.

The group A in the formulae hereinbefore and hereinafter has 1–6, preferably 1, 2, 3 or 4 C atoms. Specifically, A is preferably methyl, ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2- or 3-methylpentyl.

X is preferably —OH, —$OCH_3$, —O—$CH_2$—$CH_3$, 4-carboxypiperidino, 4-carboxymethoxypiperidino, 4-carboxymethylpiperazino, 4-carboxyethylpiperazino or is particularly preferably an amino acid or dipeptide residue which is linked to the carbonyl group via an amide linkage. If X is an amino acid or dipeptide residue, the following are particularly preferred: Ala, β-Ala, Gly, Arg and β-Ala-Asp or Sar.

The group Q is preferably —$NH_2$, —C(=NH)—$NH_2$, —$CH_2$—$NH_2$, —$CH_2$—NH— CO—alk—$NH_2$, —$CH_2$—NH—CO—Ar—C(=NH)—$NH_2$, —$CH_2NH$—CO—alk—C(=NH)—$NH_2$, —$CH_2$—NH—CO—Ar—$CH_2$—$NH_2$, $NC_2$ or CN. Q is additionally preferably —C(=NH)—S—A, —$CSNH_2$ or —C(=NH)—NHOH.

The radical —Ar— is phenylene which is bonded, preferably via its 1 and 4 positions, to the other radicals.

The group "—alk—" is preferably alkylene with 1 to 5 C atoms, particularly preferably —$CH_2$—, —$(CH_2)_2$—, —$CH(CH_3)$—, —$(CH_2)_3$—, —$(CH_2)_4$— or —$(CH_2)_5$—, The parameters m and n are preferably 1, but also furthermore 2 or 3. The variable p is preferably 0 or 1, while q and r are preferably 1.

Preferred compounds of the formula I are those in which at least one of the stated radicals, groups and/or parameters has one of the stated preferred meanings. The compounds of the formula I embrace those of the formulae Ia and Ib which correspond to the formula I but in which in Ia R is Q and R' is COX; in Ib R is COX and R' is Q;
preferred compounds have the formulae Iaa to Ian which correspond to the formula Ia but in which additionally

| | |
|---|---|
| in Iaa | Q is C(=NH)—$NH_2$; |
| in Iab | Q is C(=NH)—S—A; |
| in Iac | Q is $CSNH_2$; |
| in Iad | Q is CN; |
| in Iae | Q is $CH_2$—$NH_2$; |
| in Iaf | Q is $CH_2$—$NH_2$ in which the $NH_2$ group is substituted by an amino protective group; |
| in Iag | Q is $NO_2$ or $NH_2$; |
| in Iah | Q is $CH_2$—NH—CO—alk—$NH_2$ where "—alk—" can be straight-chain or branched; |

| | |
|---|---|
| in Iai | Q is CH$_2$—NH—CO--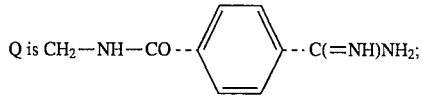--C(=NH)NH$_2$; |
| in Iaj | Q is CH$_2$—NH—CO--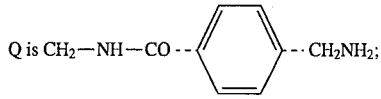--CH$_2$NH$_2$; |
| in Iak | X is β-Ala or β-Ala—Asp, where the free acid group of the amino acid residue can also be esterified, for example, with the discussed protective groups; |
| in Ial | X is OH or OA; |
| in Iam | X is a piperidine or piperazine radical substituted in the 4-position; |
| in Ian | 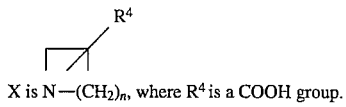 X is N—(CH$_2$)$_n$, where R$^4$ is a COOH group. |

Further preferred compounds are of the formulae Iba to Ibf which correspond to the formula Ib but in which additionally

| | |
|---|---|
| in Iba | Q is C(=NH)—NH$_2$; |
| in Ibb | Q is C(=NH)—SA or CSNH$_2$; |
| in Ibc | Q is CN, NH$_2$, NO$_2$, 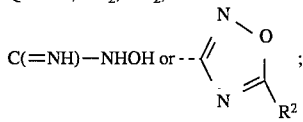 C(=NH)—NHOH or --  ; |
| in Ibd | X is Ala, β-Ala, β-Ala—Arg or one of the said amino acid or dipeptide residues esterified at the C terminus, for example, with the discussed protective groups. |
| in Ibe | 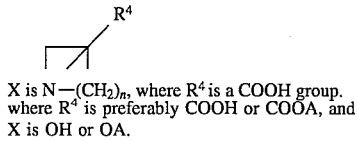 X is N—(CH$_2$)$_n$, where R$^4$ is a COOH group. where R$^4$ is preferably COOH or COOA, and |
| in Ibf | X is OH or OA. |

Further preferred compounds correspond per se to the formulae Iaa to Ian and Iba to Ibf but in them the imidazopyridine group is replaced by a 5,6,7,8-tetrahydroimidazo[1,2-a]pyridine group. Furthermore, the invention includes all those compounds which have an NH$_2$ group, this NH$_2$ group being provided, however, with a protective group known per se.

The compounds of the formula I and the starting materials for preparing them are moreover prepared by methods known per se, as are described in the literature (for example in the standard works such as Houben-Weyl, Methoden der organisthen Chemie [Methods or Organic Chemistry], Georg-Thieme Verlag, Stuttgart; furthermore J. March, Adv. Org. Chem., 3rd Ed. (1985), J. Wiley & Sons), specifically under reaction conditions known and suitable for the said reactions. It is moreover possible also to make use of variants which are known per se but not mentioned in detail here.

The starting materials can, if required, also be formed in situ so that they are not isolated from the reaction mixture but immediately reacted further to give the compounds of the formula I.

The compounds of the formula I can be obtained by liberating them from their functional derivatives by solvolysis, in particular hydrolysis, or by hydrogenolysis.

Preferred starting materials for the solvolysis or hydrogenolysis are those which otherwise correspond to the formula I but which contain corresponding protected amino and/or hydroxyl groups in place of one or more free amino and/or hydroxyl groups, preferably those which carry an amino protective group in place of a H atom which is bonded to an N atom, in particular those which carry an R'-N group, in which R' is an areinc protective group, in place of an HN group, and/or those which carry a hydroxyl protective group in place of the H atom of a hydroxyl group, for example those which correspond to the formula I but which carry a —COOR" group, in which R" is a hydroxyl protective group, in place of a —COOK group.

Several—identical or different—protected amino and/or hydroxyl groups may be present in the molecule of the starting compound. If the protective groups which are present differ from each other, they may, in many cases, be eliminated selectively.

The expression "amino protective group" is well known and refers to groups which are suitable for protecting (blocking) an amino group from chemical reactions but which can easily be removed once the desired chemical reaction has been carried out at another site in the molecule. Especially typical of such groups are unsubstituted or substituted acyl, aryl (e.g. 2,4-dinitrophenyl (DNP)), aralkoxymethyl (e.g. benzyloxymethyl (BOM)) or aralkyl groups (e.g. benzyl, 4-nitrobenzyl or triphenylmethyl). Since the amino protective groups are removed after the desired reaction (or sequence of reactions), their nature and size is otherwise not critical; nevertheless, those having 1–20, in particular 1–8, C atoms are preferred. In connection with the present process, the expression "acyl group" is to be interpreted in its widest sense. It embraces acyl groups derived from aliphatic, araliphatic, aromatic or heterocyclic carboxylic acids or sulfonic acids, and, in particular, alkoxycarbonyl, aryloxycarbonyl and, especially, aralkoxycarbonyl groups. Examples of acyl groups of this kind are alkanoyl, such as acetyl, propionyl or butyryl; aralkanoyl, such as phenylacetyl; aroyl, such as benzoyl or toluyl; aryloxyalkanoyl, such as phenoxyacetyl; alkoxycarbonyl, such as methoxycarbonyl, ethoxycarbonyl, 2,2,2-trichloroethoxycarbonyl, isopropoxycarbonyl, tert-butoxycarbonyl (BOC) or 2-iodoethoxycarbonyl; aralkyloxycarbonyl, such as benzyloxycarbonyl (CBZ), 4-methoxybenzyloxycarbonyl or 9-fluorenylmethoxycarbonyl (FMOC). Amino protective groups which are preferred are BOC, DNP and BOM, and, in addition, CBZ, benzyl and acetyl.

The expression "hydroxyl protective group" is likewise well known and refers to groups which are suitable for protecting a hydroxyl group from chemical reactions but which are readily removed once the desired chemical reaction has been carried out at another site in the molecule. Typical of such groups are the abovementioned unsubstituted or substituted aryl, aralkyl or acyl groups, as are alkyl groups. The nature and size of the hydroxyl protective groups is not critical since they are removed again after the desired chemical reaction or sequence of reactions Protective groups having 1–20, in particular 1–10, C atoms are preferred. Examples of hydroxyl protective groups are, inter alia, tert-butyl, benzyl, p-nitrobenzoyl, p-toluenesulfonyl and acetyl, with benzyl and acetyl being particularly preferred.

The functional derivatives of the compounds of the formula I, which are to be used as starting materials, may be prepared by customary methods as described, for example, in the said standard works and patent applications, for example by reacting compounds which conformto the formulae II and III, with, however, at least one of these compounds containing a protective group in place of a H atom.

The liberation of the compounds of the formula I from their functional derivatives is, for example, achieved—depending on the protective group used—with strong acids, expediently with trifluoroacetic acid or perchloric acid, but also with other strong inorganic acids, such as hydrochloric acid or sulfuric acid, strong organic carboxylic acids, such as trichloroacetic acid, or sulfonic acids, such as benzenesulfonic acid or p-toluenesulfonic acid. It is possible, but not always necessary, for an inert solvent to be present in addition.

Inert solvents which are suitable are preferably organic, for example carboxylic acids, such as acetic acid, ethers, such as tetrahydrofuran (THF) or dioxane, amides, such as dimethylformamide (DMF), halogenated hydrocarbons, such as dichloromethane, and, in addition, alcohols, such as methanol, ethanol or isopropanol and also water. In addition, mixtures of the abovementioned solvents are suitable. Trifluoroacetic acid is preferably used in excess without the addition of any further solvent. Perchloric acid is preferably used in the form of a mixture of acetic acid and 70% perchloric acid in a ratio of 9:1. The reaction temperatures for the cleavage are expediently about 0° to about 50°, preferably between 15° and 30° (room temperature).

The BOC group can be eliminated, e.g. preferably using 40% trifluoroacetic acid in dichloromethane or using about from 3 to 5 N HCl in dioxane at 15°–60°, and the FMOC group using an approximately 5–20% solution of dimethylamine, diethylamine or piperidine in DMF at 15°–50°. Elimination of the DNP group is also achieved, for example, using an approximately 3–10% solution of 2-mercaptoethanol in DMF/water at 15°–30°.

Protective groups which can be removed by hydrogenolysis (e.g. BOM, CBZ or benzyl) can be eliminated, for example, by treating with hydrogen in the presence of a catalyst (e.g. a precious metal catalyst such as palladium, expediently on a support such as carbon). Suitable solvents in this case are those indicated above, in particular, for example, alcohols, such as methanol or ethanol, or amides, such as DMF. As a rule, the hydrogenolysis is carried out at temperatures of about 0° to 100° and under pressures of between about 1 and 200 bar, preferably at 20°–30° and at 1–10 bar. Hydrogenolysis of the CBZ group is readily achieved, for example, on 5–10% Pd—C in methanol at 20°–30°.

It is furthermore possible, for example, to carry out a hydrogenolytic conversion of a 1,2,4-oxadiazolin-5-on-3-yl or a 5-alkyl-1,2,4-oxadiazol-3-yl group into an amidino group by catalytic hydrogenation.

Compounds of the formula I can also preferably be obtained by reacting a compound of the formula II with a pyridine derivative of the formula III. Preferably used for this purpose are the methods, which are known per se, of nucleophilic substitution and/or N-alkylation of amines, and the reactions for amide formation.

The leaving group Y of the formula II is preferably Cl, Br, I or OH or a group which can be derived therefrom, such as, for example, the trifluoromethanesulfonyloxy, toluenesulfonyloxy or methanesulfonyloxy group.

The reaction is preferably carried out in the presence of an additional base, for example an alkali metal or alkaline earth metal hydroxide or carbonate, such as sodium, potassium or calcium hydroxide, or sodium, potassium or calcium carbonate, in an inert solvent, for example a halogenated hydrocarbon, such as dichloromethane, an ether, such as THF or dioxane, an amide, such as DMF or dimethylacetamide, or a nitrile, such as acetonitrile, at temperatures of about $-10°$ to 200°, preferably of 0° to 120°. If the leaving group Y is different from I, it is advisable to add an iodide such as potassium iodide.

The starting materials of the formula II are, as a rule, known or can be prepared in analogy to known compounds. They can be prepared, for example, by reacting a substituted benzene derivative with acid chlorides of the formula $Ci—CO—CH_2—Y$ (Friedel—Crafts acylation) in the presence of a Lewis acid. The compounds of the formula II can furthermore be obtained by, for example, starting from an acetophenone which is appropriately substituted on the methyl group, modifying the phenyl ring by electrophilic substitution, or by converting a radical R' into another radical R' by, for example, esterifying an acid group or linking it to an amino acid or a dipeptide, or by, for example, converting a CN group into a $CSNH_2$ group.

It is furthermore possible to convert a radical Y in a compound of the formula II into another radical Y, for example by reacting an OH group (Y=OH) with $SOCl_2$, $SOBr_2$, methanesulfonyl chloride or p-toluenesulfonyl chloride.

The pyridine derivatives of the formula III are, as a rule, known and commercially obtainable.

The compounds of the formula II are reacted with pyridines of the formula III in a manner known per se, preferably in a protic or aprotic polar inert solvent at temperatures of 20° to the boiling point of the solvent. The reaction times are 10 rain to 24 h, preferably 2 h to 10 h.

Particularly suitable solvents are also alcohols such as methanol, ethanol, isopropanol, n-butanol or tert-butanol; ethers such as diethyl ether, diisopropyl ether, tetrahydrofuran (THF) or dioxane; glycol ethers such as ethylene glycol monomethyl or monoethyl ether (methylglycol or ethylglycol), ethylene glycol dimethyl ether (diglyme); ketones such as acetone or butanone; nitriles such as acetonitrile; nitro compounds such as nitromethane or nitrobenzene; esters such as ethyl acetate or hexamethylphosphoric triamide; sulfoxides such as dimethyl sulfoxide (DMSO); chlorinated hydrocarbons such as dichloromethane, chloroform, trichloroethylene, 1,2-dichloroethane or carbon tetrachloride; hydrocarbons such as benzene, toluene or xylene. Also suitable are mixtures of these solvents with one another. N-methylpyrrolidone is particularly suitable.

Derivatives with free primary or secondary amino groups are preferably reacted in protected form. Suitable protective groups are those mentioned previously, It is furthermore possible to obtain a compound of the formula I by converting a radical R and/or R' in a compound of the formula I into another radical R and/or R'.

In particular, cyano groups can be reduced to aminomethyl groups or converted into amidino groups, carboxyl groups can be esterified, ester groups can be cleaved, benzyl groups can be removed hydrogenolytically, and aminomethyl groups can be converted into guanidinomethyl groups.

Cyano groups can expediently be reduced to aminomethyl groups by catalytic hydrogenation, e.g. on Raney nickel at temperatures of 0° to 100°, preferably 10° to 30°, and under pressures of 1 to 200 bar, preferably under standard pressure, in an inert solvent, e.g. in a lower alcohol, such as methanol or ethanol, expediently in the presence of ammonia. If the reaction is carried out, for example, at about 20° and 1 bar, benzyl ester or N-benzyl groups present in the starting material are then preserved. If it is desired to cleave these groups by hydrogenolysis, it is then expedient to use a precious metal catalyst, preferably Pd-carbon, it being possible to add an acid such as acetic acid and also water to the solution.

In order to prepare an amidine of the formula I, ammonia can be added to a nitrile of the formula I. The addition is preferably effected in several steps by, in a manner known per se, a) converting the nitrile with $H_2S$ into a thioamide which is converted with an alkylating agent, e.g. $CH_3I$, into the corresponding S-alkylimidothio ester which, for its part, reacts with $NH_3$ to yield the amidine, b) converting the nitrile with an alcohol, e.g. ethanol, in the presence of HCl into the corresponding imido ester and treating the latter with ammonia, or c) reacting the nitrile with lithium bis (trimethylsilyl)amide and subsequently hydrolyzing the product.

The corresponding N-hydroxyamidine s of the formula I can be obtained analogously from the nitriles when hydroxylamine is used in place of ammonia in method a) or b).

For the esterification, an acid of the formula I can be treated with an excess of an alcohol, preferably in the presence of a strong acid such as hydrochloric acid or sulfuric acid at temperatures of 0° to 100°, preferably 20° to 50°.

It is furthermore possible to convert N-hydroxyamidines by reaction with aliphatic carbonyl chlorides into 1,2,4-oxadiazoles or 1,2,4-oxadiazolinones and then to convert the latter by catalytic hydrogenation, for example on Raney Ni, Pd/C or $PtO_2$, preferably in MEOH, dioxane, glacial acetic acid, glacial acetic/acetic anhydride or DMF, into amidines.

Conversely, an ester of the formula I can be converted into the corresponding acid of the formula I, preferably by solvolysis by one of the methods mentioned above, for example with NaOH or KOH in water/dioxane at temperatures of 0° to 40°, preferably 10° to 30°.

A base of the formula I can be converted with an acid into the associated acid addition salt. Acids which are especially suitable for this reaction are those which yield physiologically harmless salts. Thus, inorganic acids may be used, for example sulfuric acid, nitric acid, hydrohalic acids, such as hydrochloric acid or hydrobromic acid, phosphoric acids, such as orthophosphoric acid, or sulfamic acid, and, in addition, organic acids, in particular aliphatic, alicyclic, araliphatic, aromatic or heterocyclic monobasic or polybasic carboxylic, sulfonic or sulfuric acids, e.g. formic acid, acetic acid, trifluoroacetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methanesulfonic acid, ethanesulfonic acid, ethanedisulfonic acid, 2-hydroxyethanesulfonic acid, benzenesulfonic acid, p-toluenesulfonic acid, naphthalenemono-sulfonic acid, naphthalenedisulfonic acid and laurylsulfuric acid. Salts with physiologically unacceptable acids, e.g. picrates, may be used for isolating and/or purifying the compounds of the formula I.

If desired, the free bases of the formula I can be liberated from their salts by treatment with strong bases such as sodium or potassium hydroxide, or sodium or potassium carbonate.

It is also possible to convert carboxylic acids of the formula I by reaction with appropriate bases into their metal or ammonium salts, for example their sodium, potassium or calcium salts.

The compounds of the formula I, principally the tetrahydro derivatives may contain one or more chiral centers and may therefore exist in racemic or optically active form. Racemates which have been obtained can be resolved mechanically or chemically into the enantiomers using methods which are known per se. Diastereomers are preferably formed from the racemic mixture by reaction with an optically active resolving agent. Suitable resolving agents are, for example, optically active acids, such as the D and L forms of tartaric acid, diacetyltartaric acid, dibenzoyltartaric acid, mandelic acid, malic acid or lactic acid, or the various optically active camphorsulfonic acids, such as β-camphor-sulfonic acid.

It is also advantageous to resolve the enantiomers using a column which is packed with an optically active resolving agent (e.g.,dinitrobenzoylphenylglycine); a mixture of hexane/isopropanol/acetonitrile is an example of a suitable eluent.

It is also, of course, possible to obtain optically active compounds of the formula I by the methods described above by using starting materials (for example those of the formula II) which are already optically active.

The novel compounds of the formula I and their physiologically acceptable salts can be used for preparing pharmaceutical preparations by bringing them into a suitable dosage formtogether with at least one excipient or auxiliary substance and, if desired, together with one or more additional active compound(s). The preparations thus obtained can be employed as medicaments in human or veterinary medicine. Suitable excipient substances are organic or inorganic substances which are suitable for enteral (e.g., oral or rectal) or parenteral administration or for administration in the form of an inhalation spray and which do not react with the novel compounds, for example water, vegetable oils, benzyl alcohols, polyethylene glycols, glycerol triacetate and other fatty acid glycerides, gelatin, soya lecithin, carbohydrates, such as lactose or starch, magnesium stearate, talc and cellulose. Tablets, coated tablets, capsules, syrups, juices or drops are used, in particular, for oral administration; lacquered tablets and capsules having enteric coatings or capsule shells are especially of interest. Suppositories are used for rectal administration, and solutions, preferably oily or aqueous solutions, and, in addition, suspensions, emulsions or implants are used for parenteral administration.

For administration as an inhalation spray, sprays can be used which contain the active compound either dissolved or suspended in a propellent gas mixture. The active compound is expediently used in this context in micronized form, it being possible for one or more additional physiologically tolerated solvents, e.g,. ethanol, to be present. Inhalation solutions can be administered with the aid of customary inhalers, The novel compounds can also be lyophilized and the resulting lyophilizates used, for example, for producing injection preparations. The preparations indicated can be sterilized and/or can contain auxiliary substances, such as preservatives, stabilizers and/or wetting agents, emulsifiers, salts for influencing the osmotic pressure, buffering substances, colorants and/or flavorings. If desired, they can also contain one or more additional active compounds, e.g., one or more vitamins.

As a rule, the substances according to the invention are administered in analogy with other known, commercially available, drugs, in particular, however, in analogy with the compounds described in EP-A-459256, preferably in dosages of about 5 mg-1 g, in particular of 50–500 mg, per dosage unit. The daily dosage is preferably about 0.1–20 mg/kg, in particular 1–10 mg/kg, of body weight. However, the special dose for each particular patient depends on a wide variety of factors, for example, on the activity of the special compound employed, on the age, body weight, general state of health and sex, on the food, on the time and route of administration, on the speed of excretion, on the combination of drugs being employed, and on the severity of the particular disease to which the therapy applies. Oral administration is preferred.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, cited above and below, and of corresponding application German P 44 05 378.9, filed Feb. 19, 1994, are hereby incorporated by reference.

Hereinbefore and hereinafter, all temperatures are indicated in ° C. and parts in parts by weight. In the following examples, "customary working-up" denotes: water is added if necessary, the pH is adjusted to values of between 2 and 8, depending on the constitution of the final product, the mixture is extracted with ethyl acetate or dichloromethane, the phases are separated, the organic phase is dried over sodium sulfate and concentrated by evaporation, and the product is purified by chromatography on silica gel and/or by crystallization. Where molecular masses are stated, conventional mass spectroscopic values are indicated by "M", and fast atom bombardment values, called FAB values, are indicated by "M+1".

EXAMPLES

Example 1

A solution of 0.54 g of tert-butyl 3-[4-(7-amidinoimidazo [1,2-a]pyridin-2-yl)benzamido]propionate [obtainable as in Example 2]in 6 ml of trifluoroacetic acid is stirred at room temperature for 1 h. The solution is mixed with diethyl ether and evaporated to dryness in vacuo. The resulting product is triturated with diethyl ether and again dried in vacuo. 3-[4-(7-amidinoimidazo[1,2-a]pyridin-2-yl)benzamido]propionic acid bistrifluoroacetate hydrate is obtained, m.p. 307°.

The following is obtained analogously by reaction with trifluoroacetic acid starting from tert-butyl 3-[4-(6-amidinoimidazo[1,2-a]pyridin-2-yl)benzamido]propionate:
3-[4-(6-amidinoimidazo[1,2-a]pyridin-2-yl)benzamido]propionic acid bistrifluoroacetate.

Example 2

A solution of 1.8 g of tert-butyl 3-[4-(7-methylsulfimidoimidazo[1,2-a]pyridin-2-yl)benzamido]propionate in the form of the hydroiodide [obtainable as in Example 4] are dissolved in 150 ml of methanol and stirred in the presence of 1.5 g of ammonium acetate at room temperature for 3 days. Customary working-up after evaporation results in tert-butyl 3-[4-(7-amidinoimidazo[1,2-a]-pyridin-2-yl)benzamido]propionate, m.p. 172°.

The following are obtained analogously starting from tert-butyl 3-[4-(6-methylsulfimidoimidazo[1,2-a]pyridin-2-yl)benzamido]propionate in the form of the hydroiodide:
tert-butyl 3-[4-(6-amidinoimidazo[1,2-a]pyridin-2-yl)benzamido]propionate; and from tert-butyl 3- [4-(8-methylsulfimidoimidazo[1,2-a]pyridin-2-yl)benzamido]propionate in the form of the hydroiodide:
tert-butyl 3-[4-(8-amidinoimidazo[1,2-a]pyridin-2-yl)benzamido]propionate.

Example 3

1.5 g of tert-butyl 3-[4-(7-cyanoimidazo[1,2-a]pyridin-2-yl)benzamido]propionate [obtainable as in Example 5] are dissolved in a solvent mixture consisting of 22 ml of pyridine, 2.7 ml of triethylamine and 3 ml of DMF, and the mixture is stirred while cooling in ice for 1.5 h, continuously passing H$_2$S gas in during this period. The reaction mixture is then stirred at room temperature for 20 h. The customary working-up after evaporation results in tert-butyl 3-[4-(7-thiocarbamoylimidazo[1,2-a]pyridin-2-yl)benzamido] propionate, m.p. 215° (decomposition).

Example 4

Tert-butyl 3-[4-(7-thiocarbamoylimidazo[1,2-a]pyridin-2-yl)benzamido]propionate [obtainable as in Example 3] are suspended in 65 ml of acetone and, after addition of 3.3 ml of methyl iodide, stirred at room temperature for 48 h. The precipitate is filtered off with suction and washed with 20 ml of acetone and dried. Tert-butyl 3-[4-(7-methylsulfimidoimidazo[1,2-a]pyridin-2-yl)benzamido]propionate hydroiodide is obtained, m.p. 193° (decomposition).

Example 5

8.5 g of 2-amino-4-cyanopyridine and 27.5 g of 4-bromoacetylbenzoic acid are boiled in 260 ml of ethanol for 20 h. After cooling, the precipitate is filtered off with suction and subjected to the customary working-up. 4-(7-Cyanoimidazo[1,2-a]pyridin-2-yl)benzoic acid hydrobromide is obtained, m.p. >310°.

The following are obtained analogously by reacting 4-bromoacetylbenzoic acid
with 2-amino-3-cyanopyridine:
 4-(8-cyanoimidazo[1,2-a]pyridin-2-yl)benzoic acid hydrobromide;
with 2-amino-5-cyanopyridine:
 4-(6-cyanoimidazo[1,2-a]pyridin-2-yl) benzoic acid hydrobromide.

The following is obtained analogously by reacting 3-bromoacetylbenzoic acid with 2-amino-3-cyanopyridine:
 3-(8-cyanoimidazo[1,2-a]pyridin-2-yl) benzoic acid hydrobromide.

Example 6

6.6 g of 4-(7-cyanoimidazo[1,2-a]pyridin-2-yl)benzoic acid [obtainable as in Example 5]in 100 ml of dichloromethane and 25 ml of DMF are stirred with 4.5 g of β-alanine tert-butyl ester in the presence of 5.25 g of N-(3-dimethylaminopropyl)-N'-ethylcarbodiimide and 6 ml of N-methylmorpholine at room temperature for 20 h. This is followed by extraction 3–4 times with 30 ml of water each time, evaporation and the customary working-up. Tert-butyl 3-[4-(7-cyanoimidazo[1,2-a]pyridin-2-yl)benzamido]propionate is obtained, m.p. 212° (decomposition).

The following are obtained analogously by reaction
of 4-(6-cyanoimidazo[1,2-a]pyridin-2-yl)benzoic acid with tert-butyl piperidine-4 -carboxylate:
 tert-butyl 1-[4-(6-cyanoimidazo[1,2-a]pyridin-2-yl)-benzoyl]piperidine-4-carboxylate, m.p. 247° (decomposition);
of 4-(6-amidinoimidazo[1,2-a]pyridin-2-yl)benzoic acid with tert-butyl piperidine-4-carboxylate:

tert-butyl 1-[4-(6-amidinoimidazo[1,2-a]pyridin-2-yl)benzoyl]piperidine-4-carboxylate;
of 4-(7-amidinoimidazo[1,2-a]pyridin-2-yl)benzoic acid with tert-butyl piperidine-4-carboxylate:
tert-butyl 1-[4-(7-amidinoimidazo[1,2-a]pyridin-2-yl)benzoyl]piperidine-4-carboxylate;
of 4-(8-amidinoimidazo[1,2-a]pyridin-2-yl)benzoic acid with tert-butyl piperidine-4-carboxylate:
tert-butyl 1- [4-(8-amidinoimidazo[1,2-a]pyridin-2-yl)benzoyl]piperidine-4-carboxylate.

Example 7

1.4 g of tert.-butyl 1-[4-(6-cyanoimidazo[1,2-a]pyridin-2-yl)benzoyl]piperidine-4-carboxylate [obtainable as in Example 6]in 140 ml of methanol are hydrogenated in the presence of 1.1 g of di-tert-butyl dicarbonate on Pd/carbon (5%). The catalyst is then filtered off, and the reaction mixture is concentrated and subjected to the customary working-up. Chromatography on silica gel with ethyl acetate results in tert-butyl 1-[4-(6-tert-butoxycarbonylaminomethylimidazo[1,2-a]pyridin-2-yl)benzoyl]-piperidine-4-carboxylate, m.p. 158°–162°.

Elution with dichloromethane/methanol in the chromatographic separation additionally results in the more polar component:
tert-butyl 1-[4-(6-tert-butoxycarbonylaminomethyl-5,6,7,8-tetrahydroimidazo[1,2-a]pyridin-2-yl)benzoyl]-piperidine-4-carboxylate.

The following are obtained analogously starting
from 4-(7-cyanoimidazo[1,2-a]pyridin-2-yl)benzoic acid:
  tert-butyl 4-(7-tert-butoxycarbonylaminomethylimidazo[1,2-a]pyridin-2-yl)benzoate and
  tert-butyl 4-(7-tert-butoxycarbonylaminomethyl-5,6,7,8-tetrahydroimidazo[1,2-a]pyridin-2-yl)benzoate;
from 4-(8-cyanoimidazo[1,2-a]pyridin-2-yl)benzoic acid:
  tert-butyl 4-(8-tert-butoxycarbonylaminomethylimidazo-[1,2 -a]pyridin-2-yl)benzoate and
  tert-butyl 4-(8-tert-butoxycarbonylaminomethyl-5,6,7,8-tetrahydroimidazo[1,2-a]pyridin-2-yl)benzoate;
from 4-(6-cyanoimidazo[1,2-a]pyridin-2-yl)benzoic acid:
  tert-butyl 4-(6-tert-butoxycarbonylaminomethylimidazo [1,2 -a]pyridin-2-yl)benzoate and tert-butyl 4-(6-tert-butoxycarbonylaminomethyl-5,6,7,8-tetrahydroimidazo[1,2-a]pyridin-2-yl)benzoate;
from 3-(8-cyanoimidazo[1,2-a]pyridin-2-yl)benzoic acid:
  tert-butyl 3-(8-tert-butoxycarbonylaminomethylimidazo [1,2-a]pyridin-2-yl)benzoate and
  tert-butyl 3-(8-tert-butoxycarbonylaminomethyl-5,6,7,8,-tetrahydroimidazo[1,2-a]pyridin-2-yl)benzoate;

Example 8

A solution of 0.64 g of tert-butyl 1-[4-(6-tert-butoxycarbonylaminomethylimidazo[1,2-a]pyridin-2-yl)benzoyl]-piperidine-4-carboxylate [obtainable as in Example 7] in 7 ml of trifluoroacetic acid is stirred at room temperature for 0.5 h. Then 50 ml of toluene are added, the solvent is removed, and the residue is triturated with diethyl ether. Drying results in 1-[4-(6-aminomethylimidazo[1,2-a]pyridin-2-yl)benzoyl] piperidine-4-carboxylic acid bistrifluoroacetate, m.p. 148° (decomposition).

The following are obtained analogously by treatment with trifluoroacetic acid:

from tert-butyl 1-[4-(7-tert-butoxycarbonylaminomethylimidazo[1,2-a]pyridin-2-yl)benzoyl]piperidine-4-carboxylate:
  1-[4-(7-aminomethylimidazo[1,2-a]pyridin-2-yl)benzoyl]piperidine-4-carboxylic acid bistrifluoroacetate;
from tert-butyl 1-[4-(7-tert-butoxycarbonylaminomethyl-5,6,7,8-tetrahydroimidazo[1,2-a]pyridin-2-yl)benzoyl]-piperidine-4-carboxylate:
  1-[4-(7-aminomethyl-5,6,7,8-tetrahydroimidazo[1,2-a] pyridin-2-yl)benzoyl]piperidine-4-carboxylic acid bistrifluoroacetate;
from tert-butyl 1-[4-(6-tert-butoxycarbonylaminomethyl-5,6,7,8-tetrahydroimidazo[1,2-a]pyridin-2-yl)benzoyl]-piperidine-4-carboxylate:
  1-[4-(6-aminomethyl-5,6,7,8-tetrahydroimidazo[1,2-a] pyridin-2-yl)benzoyl]piperidine-4-carboxylic acid bistrifluoroacetate;
from tert-butyl 3- [4-(7-tert-butoxycarbonylaminomethylimidazo[1,2-a ]pyridin-2-yl)benzamido]propionate:
  3-[4-(7-aminomethylimidazo[1,2-a]pyridin-2-yl)benzamido]propionic acid bistrifluoroacetate;
from tert-butyl 3-[4-(7-tert-butoxycarbonylaminomethyl-5,6,7,8-tetrahydroimidazo[1,2-a]pyridin-2-yl)benzamido] propionate:
  3-[4-(7-aminomethyl-5,6,7,8-tetrahydroimidazo[1,2-a] pyridin-2-yl)benzamido]propionic acid bistrifluoroacetate, m.p. 183° (decomposition);
from tert-butyl 4-(7-tert-butoxycarbonylaminomethylimidazo[1,2-a]pyridin-2-yl)benzoate:
  4-(7-aminomethylimidazo[1,2-a]pyridin-2-yl)benzoic acid bistrifluoroacetate;
from tert-butyl 4-(7-tert-butoxycarbonylaminomethyl-5,6,7,8-tetrahydroimidazo[1,2-a]pyridin-2-yl)benzoate:
  4-(7-aminomethyl-5,6,7,8-tetrahydroimidazo[1,2-a]pyridin-2-yl)benzoic acid bistrifluoroacetate;
from tert-butyl 4-(8-tert-butoxycarbonylaminomethylimidazo[1,2-a ]pyridin-2-yl)benzoate:
  4-(8-aminomethylimidazo[1,2-a]pyridin-2-yl)benzoic acid bistrifluoroacetate;
from tert-butyl 4-(8-tert-butoxycarbonylaminomethyl-5,6,7,8-tetrahydroimidazo[1,2-a ]pyridin-2-yl)benzoate:
  4-(8-aminomethyl-5,6,7,8-tetrahydroimidazo[1,2-a]pyridin-2-yl)benzoic acid bistrifluoroacetate;
from tert-butyl 4-(6-tert-butoxycarbonylaminomethylimidazo[1,2-a]pyridin-2-yl)benzoate:
  4-(6-aminomethylimidazo[1,2-a]pyridin-2-yl)benzoic acid bistrifluoroacetate;
from tert-butyl 4-(6-tert-butoxycarbonylaminomethyl-5,6,7,8-tetrahydroimidazo[1,2-a]pyridin-2-yl)benzoate:
  4-(6-aminomethyl-5,6,7,8-tetrahydroimidazo[1,2-a]pyridin-2 -yl)benzoic acid bistrifluoroacetate;
from tert-butyl 3-(8-tert-butoxycarbonylaminomethylimidazo[1,2-a]pyridin-2-yl)benzoate:
  3-(8-aminomethylimidazo[1,2-a]pyridin-2-yl)benzoic acid bistrifluoroacetate;
from tert-butyl 3-(8-tert-butoxycarbonylaminomethyl-5,6,7,8-tetrahydroimidazo[1,2-a]pyridin-2-yl)benzoate:
  3-(8-aminomethyl-5,6,7,8-tetrahydroimidazo[1,2-a]pyridin-2-yl)benzoic acid bistrifluoroacetate.

Example 9

In analogy to Example 7, tert-butyl 3-[4-(7-tert-butoxycarbonylaminomethylimidazo[1,2-a]pyridin-2-yl)benzoyl]-piperidine-4-carboxylate is obtained starting from tertbutyl 3-[4-(7-cyanoimidazo[1,2-a]pyridin-2-yl)benzoyl]-piperidine-4-carboxylate [obtainable as in Example 6] after reaction with di-tert-butyl dicarbonate and hydrogenation on Pd/carbon (5%).

Additionally obtained as more polar component is tert-butyl 3-[4-(7-tert-butoxycarbonylaminomethylbutyl 5,6,7,8-tetrahydroimidazo [1,2-a]pyridin-2-yl)benzoyl]-piperidine-4-carboxylate, M+1:498 (FAB).

Example 10

In analogy to Example 5, 4-(8-aminoimidazo[1,2-a]pyridinyl)benzoic acid hydrobromide, m.p. >280° (decomposition) (M: 253), is obtained starting from 2,3-diaminopyridine by reaction with 4-bromoacetylbenzoic acid.

The following is obtained analogously:
3-(8-aminoimidazo[1,2-a]pyridin-2-yl)benzoic acid hydrobromide, m.p. >300° (decomposition) (M: 253), from 2,3-diaminopyridine by reaction with 3-bromoacetylbenzoic acid.

Example 11

2.2 g of 4-(8-aminoimidazo[1,2-a]pyridin-2-yl)benzoic acid hydrobromide are dissolved in 100 ml of DMF and, after addition of one equivalent of tert-butyloxycarbonyl azide, stirred at room temperature for 2 h. The customary working-up results in 4-(8-tert-butoxycarbonylaminoimidazo[1,2-a]pyridin-2-yl)benzoic acid hydrobromide.

The following is obtained analogously
from 3-(8-aminoimidazo[1,2-a]pyridin-2-yl)benzoic acid hydrobromide: 3-(8-tert-butoxycarbonylaminoimidazo[1,2-a]pyridin-2-yl)benzoic acid hydrobromide.

Example 12

In analogy to Example 6 the following is obtained, starting from 4-(8-BOC-aminoimidazo[1,2-a]pyridin-2-yl)benzoic acid [obtainable as in Example 11] by reaction with β-alanine tert-butyl ester in the presence of 5.25 g of N-(3-dimethylaminopropyl)-N'-ethylcarbodiimide and 6 ml of N-methylmorpholine at room temperature and after the customary working-up: tert-butyl 3-[4-(8-BOC-aminoimidazo[1,2-a]pyridin-2-yl)benzamido]propionate.

The following is obtained analogously by reaction with β-alanine tert-butyl ester starting
from 3-(8-BOC-aminoimidazo[1,2-a]pyridin-2-yl)benzoic acid:
   tert-butyl 3-[3-(8-BOC-aminoimidazo[1,2-a]pyridin-2-yl)benzamido]propionate.

The following are obtained analogously by reaction with β-Ala-Asp(OBut) tert-butyl ester starting
from 3-(8-BOC-aminoimidazo [1,2-a]pyridin-2-yl)benzoic acid:
   3-(8-BOC-aminoimidazo[1,2-a]pyridin-2-yl)benzoyl-β-Ala-Asp(OBut) tert-butyl ester;
from 4-(8-BOC-aminoimidazo[1,2-a]pyridin-2-yl)benzoic acid:
   4-(8-BOC-aminoimidazo[1,2-a]pyridin-2-yl)benzoyl-β-Ala-Asp(OBut) tert-butyl ester;
from 3-(8-BOC-amino-5,6,7,8-tetrahydroimidazo[1,2-a]-pyridin-2-yl)benzoic acid:
   3-(8-BOC-amino-5,6,7,8-tetrahydroimidazo[1,2-a]pyridin-2-yl)benzoyl-p-Ala-Asp(OBut) tert-butyl ester;
from 4-(8-BOC-amino-5,6,7,8-tetrahydroimidazo[1,2-a]-pyridin-2-yl)benzoic acid:
   4-(8-BOC-amino-5,6,7,8-tetrahydroimidazo[1,2-a]pyridin-2-yl)benzoyl-β-Ala-Asp(OBut) tert-butyl ester.

Example 13

In analogy to Example 8, the following are obtained after removal of the amino protective groups and hydrolysis starting
from tert-butyl 3-[4-(8-BOC-aminoimidazo[1,2-a]pyridin-2-yl)benzamido]propionate:
   3-[4-(8-aminoimidazo[1,2-a]pyridin-2-yl)benzamido] propionic acid bistrifluoroacetate, m.p. 128°–130° (decomposition);
from tert-butyl 3-[3-(8-BOC-aminoimidazo[1,2-a]pyridin-2-yl)benzamido]propionate:
   3-[3-(8-aminoimidazo[1,2-a]pyridin-2-yl)benzamido] propionic. acid bistrifluoroacetate, m.p. 260°–262° (decomposition);
from 3-(8-BOC-aminoimidazo[1,2-a]pyridin-2-yl)benzoyl-β-Ala-Asp(OBut) tert-butyl ester:
   3-(8-aminoimidazo[1,2-a]pyridin-2-yl)benzoyl-β-Ala-Asp-OH (bistrifluoroacetate), m.p. 308° (decomposition) (M: 439);
from 4-(8-BOC-aminoimidazo[1,2-a]pyridin-2-yl)benzoyl-β-Ala-Asp(OBut) tert-butyl ester:
   4-(8-aminoimidazo[1,2-a]pyridin-2-yl)benzoyl-β-Ala-Asp-OH (bistrifluoroacetate), m.p. >150° (decomposition) (M+1: 440);
from 3-(8-BOC-amino-5,6,7,8-tetrahydroimidazo[1,2-a]-pyridin-2-yl)benzoyl-β-Ala-Asp(OBut) tert-butyl ester:
   3-(8-amino-5,6,7,8-tetrahydroimidazo[1,2-a]pyridin-2-yl)benzoyl-β-Ala-Asp-OH (bistrifluoroacetate);
from 4-(8-BOC-amino-5,6,7,8-tetrahydroimidazo[1,2-a]-pyridin-2-yl)benzoyl-β-Ala-Asp(OBut) tert-butyl ester:
   4-(8-amino-5,6,7,8-tetrahydroimidazo[1,2-a]Pyridin-2-yl)benzoyl-β-Ala-Asp-OH (bistrifluoroacetate).

Example 14

In analogy to Example 1, the following imidazo [1,2-a] pyridine derivatives are obtained by hydrolysis starting from the esters from Example 6:
1-[4-(6-cyanoimidazo[1,2-a]pyridine-2-yl)benzoyl]-piperidine-4-carboxylic acid bistrifluoroacetate;
1-[4-(6-amidinoimidazo[1,2-a]pyridine-2-yl)benzoyl]-piperidine-4-carboxylic acid bistrifluoroacetate;
1-[4-(7-amidinoimidazo[1,2-a]pyridine-2-yl)benzoyl]-piperidine-4-carboxylic acid bistrifluoroacetate;
1-[4-(8-amidinoimidazo[1,2-a]pyridine-2-yl)benzoyl]-piperidine-4-carboxylic acid bistrifluoroacetate.

Example 15

One equivalent of BOC-Ala-OH is added to a solution of 2.1 g of tert-butyl 4-(8-aminomethylimidazo[1,2-a]-pyridine-2-yl)benzoate in 80 ml of dichloromethane, and the mixture is stirred in the presence of 3.25 g of N-(3-dimethylaminopropyl)-N'-ethylcarbodiimide and 6 ml of N-methylmorpholine at room temperature for 18 h. The mixture is subsequently extracted 3–4 times with water, evaporated and subjected to the customary working-up. Tert-butyl 4-[8-(BOC-Ala-aminomethyl)imidazo[1,2-a]-pyridine-2-yl)benzoate is obtained.

Analogous reaction of tert-butyl 4-(8-aminomethylimidazo[1,2-a]pyridine-2-yl)benzoate with 6-BOC-aminohexanoic acid results in tert-butyl 4-[8-(6-BOC-aminohexanoylaminomethyl)imidazo[1,2-a]pyridin-2-yl]benzoate;

Analogous reaction of tert-butyl 3-(8-aminomethylimidazo[1,2-a]pyridine-2-yl)benzoate with 6-BOC-aminohexanoic acid results in tert-butyl 3-[8-(6-BOC-aminohexanoylaminomethyl)imidazo[1,2-a]pyridin-2-yl]benzoate;

with 3-BOC-aminopropionic acid results in tert-butyl 3-[8-(3-BOC-aminopropionylaminomethyl)imidazo[1,2-a]pyridin-2-yl]benzoate.

Analogous reaction of tert-butyl 4-(8-aminomethyl-5,6,7,8-tetrahydroimidazo[1,2-a]pyridin-2-yl)benzoate with 6-BOC-aminohexanoic acid results in tert-butyl 4-[8-(6-BOC-aminohexanoylaminomethyl)-5,6,7,8-tetrahydroimidazo[1,2-a]pyridin-2-yl]benzoate;

with 3-BOC-aminopropionic acid results in tert-butyl 4-[8-(3-BOC-aminopropionylaminomethyl)-5,6,7,8-tetrahydroimidazo[1,2-a]pyridin-2-yl]benzoate;

with 4-BOC-aminomethylbenzoic acid results in tert-butyl 4-[8-(4-BOC-aminomethylbenzoylaminomethyl)-5,6,7,8-tetrahydroimidazo[1,2-a]pyridin-2-yl]benzoate.

Example 16

Reaction analogous to Example 15 of ethyl 4-(8-aminomethylimidazo[1,2-a]pyridin-2-yl)benzoate with 4-BOC-amidinobenzoic acid results in ethyl 4-[8-(4-BOC-amidinobenzoylaminomethyl)imidazo[1,2-a]pyridin-2-yl]benzoate;

of 3-[3-(8-aminomethylimidazo[1,2-a]pyridin-2-yl)benzamido]propionic acid with 3-BOC-aminopropionic acid results in 3-[3-(8-(3-BOC-aminopropionylaminomethyl)imidazo-[1,2-a]pyridin-2-yl)benzamido]propionic acid.

Example 17

In analogy to Example 8, the following compounds are obtained in the form of their trifluoroacetates by removal of the amino protective groups and hydrolysis of the tert-butyl esters with trifluoroacetic acid:

from 4-[8-(BOC-Ala-aminomethyl)imidazo[1,2-a]pyridin-2-yl]benzoic acid:

4-[8-(Ala-aminomethyl)imidazo[1,2-a]pyridin-2-yl]benzoic acid, m.p. >210° (decomposition) (M+1:339);

from 4-[8-(6-BOC-aminohexanoylaminomethyl)imidazo[1,2-a]-pyridin-2-yl]benzoic acid:

4-[8-(6-aminohexanoylaminomethyl)imidazo[1,2-a]pyridin-2-yl]benzoic acid, m.p. 234°–240°;

from 3-[8-(6-BOC-aminohexanoylaminomethyl)imidazo[1,2-a]-pyridin-2-yl]benzoic acid:

3-[8-(6-aminohexanoylaminomethyl)imidazo[1,2-a]-pyridin-2-yl]benzoic acid, m.p. 105° (decomposition);

from 3-[8-(3-BOC-aminopropionylaminomethyl)imidazo-[1,2-a]pyridin-2-yl]benzoic acid:

3-[8-(3-aminopropionylaminomethyl)imidazo[1,2-a]pyridin-2-yl]benzoic acid, m.p. 118° (decomposition);

from 4-[8-(6-BOC-aminohexanoylaminomethyl)-5,6,7,8-tetrahydroimidazo[1,2-a]pyridin-2-yl]benzoic acid:

4-[8-(6-aminohexanoylaminomethyl)-5,6,7,8-tetrahydroimidazo[1,2-a]pyridin-2-yl]benzoic acid;

from 4-[8-(3-BOC-aminopropionylaminomethyl)-5,6,7,8-tetrahydroimidazo[1,2-a]pyridin-2-yl]benzoic acid:

4-[8-(3-aminopropionylaminomethyl)-5,6,7,8-tetrahydroimidazo[1,2-a]pyridin-2-yl]benzoic acid;

from 4-[8-(4-BOC-aminomethylbenzoylaminomethyl)-5,6,7,8-tetrahydroimidazo[1,2-a]pyridin-2-yl]benzoic acid:

4-[8-(4-aminomethylbenzoylaminomethyl)-5,6,7,8-tetrahydroimidazo[1,2-a]pyridin-2-yl]benzoic acid, m.p. 150° (decomposition) (M+1:405);

from ethyl 4-[8-(4-BOC-amidinobenzoylaminomethyl)imidazo-[1,2-a]pyridin-2-yl]benzoate: ethyl 4-[8-(4-amidinobenzoylaminomethyl)imidazo[1,2-a]pyridin-2-yl]benzoate, m.p. 233°–235°;

from 3-[3-(8-(3-BOC-aminopropionylaminomethyl)imidazo-[1,2-a]pyridin-2-yl)benzamido]propionic acid:

3-[3-(8-(3-aminopropionylaminomethyl)imidazo[1,2-a]pyridin-2-yl)benzamido]propionic acid, amorphous (M+1:410).

Example 18

In analogy to Example 12, starting from 4-(8-BOC-aminomethyl-5,6,7,8-tetrahydroimidazo[1,2-a]pyridin-2-yl)benzoic acid [obtainable in analogy to Example 7] by reaction with β-alanine tert-butyl ester in the presence of 5.25 g of N-(3-dimethylaminopropyl)-N'-ethylcarbodiimide and 6 ml of N-methylmorpholine at room temperature, the following is obtained after the customary working-up:

tert-butyl 3-[4-BOC-aminomethyl-5,6,7,8-tetrahydroimidazo[1,2-a]pyridin-2-yl)benzamido]propionate.

The following are obtained analogously by reaction with β-alanine tert-butyl ester:

from 4-(7-BOC-aminomethyl-5,6,7,8-tetrahydroimidazo-[1,2-a]pyridin-2-yl)benzoic acid:

tert-butyl 3-[4-(7-BOC-aminomethyl-5,6,7,8-tetrahydroimidazo[1,2-a]pyridin-2-yl)benzamido]propionate;

from 4-(7-BOC-aminomethylimidazo[1,2-a]pyridin-2-yl)benzoic acid: tert-butyl 3-[4-(7-BOC-aminomethylimidazo[1,2-a]-pyridin-2-yl)benzamido]propionate;

from 4-(6-BOC-aminomethyl-5,6,7,8-tetrahydroimidazo-[1,2-a]pyridin-2-yl)benzoic acid:

tert-butyl 3-[4-(6-BOC-aminomethyl-5,6,7,8-tetrahydroimidazo[1,2-a]pyridin-2-yl)benzamido]propionate;

from 4-(6-BOC-aminomethylimidazo[1,2-a]pyridin-2-yl)benzoic acid:

tert-butyl 3-[4-(6-BOC-aminomethylimidazo[1,2-a]-pyridin-2-yl)benzamido]propionate;

from 3-(7-BOC-aminomethyl-5,6,7,8-tetrahydroimidazo-[1,2-a]pyridin-2-yl)benzoic acid:

tert-butyl 3-[3-(7-BOC-aminomethyl-5,6,7,8-tetrahydroimidazo[1,2-a]pyridin-2-yl)benzamido]propionate;

from 3-(7-BOC-aminomethylimidazo[1,2-a]pyridin-2-yl)benzoic acid:

tert-butyl 3-[3-(7-BOC-aminomethylimidazo[1,2-a]-pyridin-2-yl)benzamido]propionate;

from 3-(6-BOC-aminomethyl-5,6,7,8-tetrahydroimidazo-[1,2-a]pyridin-2-yl)benzoic acid:

tert-butyl 3-[3-(6-BOC-aminomethyl-5,6,7,8-tetrahydroimidazo[1,2-a]pyridin-2-yl)benzamido]propionate;

from 3-(6-BOC-aminomethylimidazo[1,2-a]pyridin-2-yl)benzoic acid:

tert-butyl 3-[3-(6-BOC-aminomethylimidazo[1,2-a]-pyridin-2-yl)benzamido]propionate.

Example 19

The following compounds are obtained in the form of their trifluoroacetates in analogy to Example 8 by removing the protective groups with trifluoroacetic acid from the compounds prepared in Example 18:

3-[4-(8-aminomethyl-5,6,7,8-tetrahydroimidazo[1,2-a]-pyridin-2-yl)benzamido]propionic acid, m.p. >87° (decomposition) (M+1:343);
3-[4-(7-aminomethyl-5,6,7,8-tetrahydroimidazo[1,2-a]-pyridin-2-yl)benzamido]propionic acid;
3-[4-(7-aminomethylimidazo[1,2-a]pyridin-2-yl)benzamido]propionic acid;
3-[4-(6-aminomethyl-5,6,7,8-tetrahydroimidazo[1,2-a]-pyridin-2-yl)benzamido]propionic acid;
3-[4-(6-aminomethylimidazo[1,2-a]pyridin-2-yl)benzamido]propionic acid;
3-[3-(7-aminomethyl-5,6,7,8-tetrahydroimidazo[1,2-a]-pyridin-2-yl)benzamido]propionic acid;
3-[3-(7-aminomethylimidazo[1,2-a]pyridin-2-yl)benzamido]propionic acid;
3-[3-(6-aminomethyl-5,6,7,8-tetrahydroimidazo[1,2-a]-pyridin-2-yl)benzamido]propionic acid;
3-[3-(6-aminomethylimidazo[1,2-a]pyridin-2-yl)benzamido]propionic acid.

Example 20

17.25 g of 2-aminopyridine-4-carboxylic acid and 28 g of 4-bromoacetylbenzonitrile are dissolved in 200 ml of N-methylpyrrolidine and heated at 160° for 7 h. After cooling, the reaction mixture is filtered and poured into 2 l of ice-water. The resulting precipitate is filtered off with suction and washed successively with 100 ml of water, 50 ml of ethanol and 50 ml of ether.

2-(4—Cyanophenyl)imidazo[1,2-a]pyridine-7-carboxylic acid hydrobromide, m. p. 3 10 o (decomposition ), is obtained.

The following are obtained analogously by reaction
of 2-aminopyridine-5-carboxylic acid with 4-bromoacetylbenzonitrile:
  2-(4-cyanophenyl)imidazo[1,2-a]pyridine-6-carboxylic acid hydrobromide, m.p. >330° (M+1:264);
of 2-aminopyridine-6-carboxylic acid with 4-bromoacetylbenzonitrile:
  2-(4-cyanophenyl)imidazo[1,2-a]pyridine-5-carboxylic acid hydrobromide;
of 2-aminopyridine-3-carboxylic acid with 4-bromoacetylbenzonitrile:
  2-(4-cyanophenyl)imidazo[1,2-a]pyridine-8-carboxylic acid hydrobromide;
of methyl 2-aminopyridin-5-carboxylate with 4-bromoacetylbenzonitrile:
  methyl 2-(4-cyanophenyl)imidazo[1,2-a]pyridine-6-carboxylate hydrobromide.

Example 21

1.32 g of 2:(4-cyanophenyl)imidazo[1,2-a]pyridine-7-carboxylic acid and 1.1 g of hydroxylamine hydrochloride are boiled in 125 ml of ethanol in the presence of 2.24 g of sodium ethanolate for 2 h. The reaction mixture is then filtered and concentrated in vacuo. The residue is dissolved in water, the solution is adjusted to pH 3 with 2N hydrochloric acid, and the resulting precipitate is filtered off with suction. Recrystallization from water/glacial acetic acid results in 2-[4-amino(hydroxyimino)methylphenyl]imidazo[1,2-a]pyridine-7-carboxylic acid, m.p. >300° (decomposition) (M+1:297).

The following are obtained analogously by reacting hydroxylamine hydrochloride
with 2-(4-cyanophenyl)imidazo[1,2-a]pyridine-6-carboxylic acid:
  2-[4-amino(hydroxyimino)methylphenyl]imidazo[1,2-a]pyridine-6-carboxylic acid;
with 2-(4-cyanophenyl)imidazo[1,2-a]pyridine-5-carboxylic acid:
  2-[4-amino(hydroxyimino)methylphenyl]imidazo[1,2-a]-pyridine-5-carboxylic acid;
with methyl 2-(4-cyanophenyl)imidazo[1,2-a]pyridine-6-carboxylate:
  methyl 2-[4-amino(hydroxyimino)methylphenyl]imidazo-[1,2-a]pyridine-6-carboxylate;
with 2-(4-cyanophenyl)imidazo[1,2-a]pyridine-8-carboxylic acid:
  2-[4-amino(hydroxyimino)methylphenyl]imidazo[1,2-a]-pyridine-8-carboxylic acid.

Example 22

5.2 g of 2-(4-cyanophenyl)imidazo[1,2-a]pyridine-7-carboxylic acid are dissolved in 60 ml of dichloromethane and 15 ml of DMF and, after addition of 2.8 g of tert-butyl 4-piperidinecarboxylate, stirred in the presence of 3.2 g of N-(3-dimethylaminopropyl)-N'-ethylcarbodiimide and 3.6 ml of N-methylmorpholine at room temperature for 24 h. The customary working-up and trituration with ether result in tert-butyl 1-[2-(4-cyanophenyl)imidazo[1,2-a]-pyridin-7-ylcarbonyl]piperidine-4-carboxylate, m.p. 209° (decomposition).

The following are obtained analogously:
from 2-(4-cyanophenyl)imidazo[1,2-a]pyridine-7-carboxylic acid with Gly tert-butyl ester:
  tert-butyl 2-[2-(4-cyanophenyl)imidazo[1,2-a]-pyridin-7-ylcarboxamido]acetate, m.p. 214°;
from 2-(4-cyanophenyl)imidazo[1,2-a]pyridine-7-carboxylic acid with β-Ala tert-butyl ester:
  tert-butyl 3-[2-(4-cyanophenyl)imidazo[1,2-a]pyridin-7-ylcarboxamido]propionate, m.p. 138°–140°;
from 2-(4-cyanophenyl)imidazo[1,2-a]pyridine-6-carboxylic acid with tert-butyl 4-piperidine carboxylate:
  tert-butyl 1-[2-(4-cyanophenyl)imidazo[1,2-a]-pyridin-6-ylcarbonyl]piperidine-4-carboxylate, m.p. 183°;
from 2-(4-cyanophenyl)imidazo[1,2-a]pyridine-6-carboxylic acid with Gly tert-butyl ester:
  tert-butyl 2-[2-(4-cyanophenyl)imidazo[1,2-a]pyridin-6-ylcarboxamido]acetate, m.p. 321° (decomposition);
from 2-(4-cyanophenyl)imidazo[1,2-a]pyridine-6-carboxylic acid with β-Ala tert-butyl ester:
  tert-butyl 2-[2-(4-cyanophenyl)imidazo[1,2-a]-pyridin-6-ylcarboxamido]propionate, m.p. 187°–190°.

Example 23

3.4 g of tert-butyl 1-[2-(4-cyanophenyl)imidazo[1,2-a]-pyridin-7-ylcarbonyl]piperidine-4-carbonyl]piperidine-4-carboxylate in a mixture containing 44 ml of pyridine, 5.4 ml of triethylamine and 6 ml of DMF are treated with gas while cooling in ice for 1.5 h. The mixture is then stirred at room temperature for 21 h. The reaction mixture is concentrated in vacuo and subjected to the customary working-up. Tert-butyl 1-[2-(4-thiocarbamoylphenyl)imidazo[1,2-a]pyridin-7-ylcarbonyl]piperidine-4-carboxylate, m.p. 170° (decomposition), is obtained.

The following are obtained analogously:

from tert-butyl 2-[2-(4-cyanophenyl)imidazo[1,2-a]-pyridin-7-ylcarboxamido]acetate:

tert-butyl 2-[2-(4-thiocarbamoylphenyl)imidazo-[1,2-a]pyridin-7-ylcarboxamido]acetate, m.p. 178°;

from tert-butyl 3-[2-(4-cyanophenyl)imidazo[1,2-a]-pyridin-7-ylcarboxamido]propionate:

tert-butyl 3-[-2-(4-thiocarbamoylphenyl)imidazo-[1,2-a]pyridin-7-ylcarboxamido]propionate, m.p. 180°;

from tert-butyl 1-[2-(4-cyanophenyl)imidazo[1,2-a]-pyridin-6-ylcarbonyl]piperidine-4-carboxylate:

tert-butyl 1-[2-(4-thiocarbamoylphenyl)imidazo-[1,2-a]pyridin-6-ylcarbonyl]piperidine-4-carboxylate, m.p. 186°;

from tert-butyl 2-[2-(4-cyanophenyl)imidazo[1,2-a]-pyridin-6-ylcarboxamido]acetate:

tert-butyl 2-[2-(4-thiocarbamoylphenyl)imidazo-[1,2-a]pyridin-6-ylcarboxamido]acetate, m.p. 278° (decomposition);

from tert-butyl 3-[2-(4-cyanophenyl)imidazo[1,2-a]-pyridin-6-ylcarboxamido]propionate:

tert-butyl 3-[2-(4-thiocarbamoylphenyl)imidazo-[1,2-a]pyridin-6-ylcarboxamido]propionate, m.p. 296°.

Example 24

3.3 g of tert-butyl 1-[2-(4-thiocarbamoylphenyl)imidazo-[1,2-a]pyridin-7-ylcarbonyl]piperidine-4-carboxylate are suspended in 140 ml of acetone, 19.2 ml of methyl iodide are added, and the mixture is stirred at room temperature for 72 h. The resulting precipitate is then filtered off with suction, washed with 30 ml of acetone and dried in vacuo. Tert-butyl 1-[2-(4-methylsulfimidoylphenyl)imidazo[1,2-a]pyridin-7-ylcarbonyl]piperidine-4-carboxylate hydroiodide, m.p. 203° (decomposition), is obtained.

The following are obtained analogously:

from tert-butyl 2-[2-(4-thiocarbamoylphenyl)imidazo-[1,2-a]pyridin-7-ylcarboxamido]acetate:

tert-butyl 2-[2-(4-methylsulfimidoylphenyl)imidazo[1,2-a]pyridin-7-ylcarboxamido]acetate hydroiodide, m.p. 158° (decomposition);

from tert-butyl 3-[2-(4-thiocarbamoylphenyl)imidazo-[1,2-a]pyridin-7-ylcarboxamido]propionate:

tert-butyl 3-[2-(4-methylsulfimidoylphenyl)imidazo[1,2-a]pyridin-7-ylcarboxamido]propionate hydroiodide, m.p. 169° (decomposition);

from tert-butyl 1-[2-(4-thiocarbamoylphenyl)imidazo-[1,2-a]pyridin-6-ylcarbonyl]piperidine-4-carboxylate:

tert-butyl 1-[2-(4-methylsulfimidoylphenyl)imidazo[1,2-a]pyridin-6-ylcarbonyl]piperidine-4-carboxylate hydroiodide, m.p. 205° (decomposition);

from tert-butyl 2-[2-(4-thiocarbamoylphenyl)imidazo-[1,2-a]pyridin-6-ylcarboxamido]acetate:

tert-butyl 2-[2-(4-methylsulfimidoylphenyl)imidazo[1,2-a]pyridin-6-ylcarboxamido]acetate hydroiodide, m.p. 185° (decomposition);

from tert-butyl 3-[2-(4-thiocarbamoylphenyl)imidazo[1,2-a]pyridin-6-ylcarboxamido]propionate:

tert-butyl 3-[2-(4-methylsulfimidoylphenyl)imidazo[1,2-a]pyridin-6-ylcarboxamido]propionate hydroiodide, m.p. 178° (decomposition).

Example 25

5.1 g of tert-butyl 1-[2-(4-methylsulfimidoylphenyl)imidazo[1,2-a]pyridin-7-ylcarbonyl]piperidine-4-carboxylate are dissolved in 400 ml of methanol, 3.3 g of ammonium acetate are added, and the mixture is stirred at room temperature for 21 h. The customary working-up and trituration with ether result in tert-butyl 1-[2-(4-amidinophenyl)imidazo[1,2-a]pyridin-7-ylcarbonyl]piperidine-4-carboxylate, m.p. 221°.

The following are obtained analogously:

from tert-butyl 2-[2-(4-methylsulfimidoylphenyl)imidazo-[1,2-a]pyridin-7-ylcarboxamido]acetate:

tert-butyl 2-[2-(4-amidinophenyl)imidazo[1,2-a]-pyridin-7-ylcarboxamido]acetate, m.p. 243°;

from tert-butyl 3-[2-(4-methylsulfimidoylphenyl)imidazo-[1,2-a]pyridin-7-ylcarboxamido]propionate:

tert-butyl 3-[2-(4-amidinophenyl)imidazo[1,2-a]-pyridin-7-ylcarboxamido]propionate, m.p. 220°;

from tert-butyl 1-[2-(4-methylsulfimidoylphenyl)imidazo-[1,2-a]pyridin-6-ylcarbonyl]piperidine-4-carboxylate:

tert-butyl 1-[2-(4-amidinophenyl)imidazo[1,2-a]pyridin-6-ylcarbonyl]piperidine-4-carboxylate, m.p. 189° (decomposition);

from tert-butyl 2-[2-(4-methylsulfimidoylphenyl)imidazo-[1,2-a]pyridin-6-ylcarboxamido]acetate:

tert-butyl 2-[2-(4-amidinophenyl)imidazo[1,2-a]-pyridin-6-ylcarboxamido]acetate, m.p. 281° (decomposition);

from tert-butyl 3-[2-(4-methylsulfimidoylphenyl)imidazo-[1,2-a]pyridin-6-ylcarboxamido]propionate:

tert-butyl 3-[2-(4-amidinophenyl)imidazo[1,2-a]-pyridin-6-ylcarboxamido]propionate, m.p. 172° (decomposition).

Example 26

0.5 g of tert-butyl 1-[2-(4-amidinophenyl)imidazo[1,2-a]-pyridin-7-ylcarbonyl]piperidine-4-carboxylate is stirred in 25 ml of ethyl acetate saturated with HCl gas at room temperature for 5 h. The precipitate is filtered off with suction, washed with 5 ml of ethyl acetate and then suspended in 30 ml of water. The suspension is adjusted to pH 10 and then stirred in an ice bath for 1 h. The precipitate is filtered off with suction, washed with 10 ml of water and dried in vacuo to result in sodium 1-[2-(4-amidinophenyl)imidazo [1,2-a]pyridin-7-ylcarbonyl]piperidine-4-carboxylate hydrate, m.p. 275° (decomposition).

The following is obtained analogously from tert-butyl 3-[2-(4-amidinophenyl)imidazo[1,2-a]-pyridin-7-ylcarboxamido]propionate:

3-[2-(4-amidinophenyl)imidazo[1,2-a]pyridin-7-ylcarboxamido]propionic acid bishydrochloride trihydrate, m.p. 283° (decomposition).

Example 27

The following are obtained in analogy to Example 1 by treatment with trifluoroacetic acid:

from tert-butyl 2-[2-(4-amidinophenyl)imidazo[1,2-a]-pyridin-7-ylcarboxamido]acetate:

2-[2-(4-amidinophenyl)imidazo[1,2-a]pyridin-7-ylcarboxamido]acetic acid bistrifluoroacetate sesquihydrate, m.p. 255° (decomposition);

from tert-butyl 1-[2-(4-amidinophenyl)imidazo[1,2-a]-pyridin-6-ylcarbonyl]piperidine-4-carboxylate:

1-[2-(4-amidinophenyl)imidazo[1,2-a]pyridin-6-ylcarbonyl]piperidine-4-carboxylic acid bistrifluoroacetate, m.p. 230° (decomposition);

from tert-butyl 2-[2-(4-amidinophenyl)imidazo[1,2-a]-pyridin-6-ylcarboxamido]acetate:

2-[2-(4-amidinophenyl)imidazo[1,2-a]pyridin-6-ylcarboxamido]acetic acid bistrifluoroacetate, m.p. 256° (decomposition);

from tert-butyl 3-[2-(4-amidinophenyl)imidazo[1,2-a]-pyridin-6-ylcarboxamido]propionate:

3-[2-(4-amidinophenyl)imidazo [1,2-a]pyridin-6-yl-carboxamido]propionic acid bistrifluoroacetate, m.p. 255° (decomposition).

Example 28

1.6 g of tert-butyl 3-(2-aminopyridin-3-ylcarboxamido)propionate [obtainable by reacting 2-aminopyridine-3-carboxylic acid with β-Ala tert-butyl ester] and 1.1 g of 4-bromoacetylbenzonitrile are boiled in 25 ml of ethanol. After the reaction is complete (TLC check) the precipitate is filtered off, washed with ethanol and dried. Tert-butyl 3-[2-(4-cyanophenyl)imidazo[1,2-a]-pyridin-8-ylcarboxamido] propionate hydrobromide, m.p. 208°–211° (M+1:391)is obtained.

The following are obtained analogously by reaction of 4-bromoacetylbenzonitrile
with tert-butyl 3-(2-aminopyridin-4-ylcarboxamido)propionate:
  tert-butyl 3-[2-(4-cyanophenyl)imidazo[1,2-a]-pyridin-7-ylcarboxamido]propionate;
with tert-butyl 2-(2-aminopyridin-4-ylcarboxamido)acetate:
  tert-butyl 2-[2-(4-cyanophenyl)imidazo[1,2-a]-pyridin-7-ylcarboxamido]acetate;
with tert-butyl 2-(2-aminopyridin-4-yl-N-methylcarboxamido)acetate:
  tert-butyl 2-[2-(4-cyanophenyl)imidazo[1,2-a]pyridin-7-yl-N-methylcarboxamido]acetate;
with tert-butyl 3-(2-aminopyridin-4-yl-N-methylcarboxamido)propionate:
  tert-butyl 3-[2-(4-cyanophenyl)imidazo[1,2-a]pyridin-7-yl-N-methylcarboxamido]propionate;
with bis-tert-butyl 2(S)-(2-aminopyridin-4-ylcarboxamido)succinate:
  bis-tert-butyl 2(S)-[2-(4-cyanophenyl)imidazo-[1,2-a]pyridin-7-ylcarboxamido]succinate;
with bis-tert-butyl 2(R)-(2-aminopyridin-4-ylcarboxamido)succinate:
  bis-tert-butyl 2(R)-[2-(4-cyanophenyl)imidazo-[1,2-a]pyridin-7-ylcarboxamido]succinate;
with tert-butyl 1-(2-aminopyridin-4-ylcarbonyl)-piperidine-4-carboxylate:
  tert-butyl 1-[2-(4-cyanophenyl)imidazo[1,2-a]-pyridin-7-ylcarbonyl]piperidine-4-carboxylate;
with 1-(2-aminopyridin-4-ylcarbonyl]-4-(tert-butoxycarbonylmethoxy)piperidine:
  1-[2-(4-cyanophenyl)imidazo[1,2-a]pyridin-7-yl-carbonyl]-4-(tert-butoxycarbonylmethoxy)piperidine;
with 1-(2-aminopyridin-4-ylcarbonyl]-4-(tert-butoxycarbonylmethyl)piperazine:
  1-[2-(4-cyanophenyl )imidazo[1,2-a]pyridin-7-yl-carbonyl]-4-(tert-butyloxycarbonylmethyl)piperazine;
with 1-(2-aminopyridin-4-ylcarbonyl)-4-[2-(tert-butoxycarbonyl)ethyl]piperazine:
  1-[2-(4-cyanophenyl)imidazo[1,2-a]pyridin-7-yl-carbonyl]-4-[2-(tert-butoxycarbonyl)ethyl ]piperazine.

Example 29

0.5 g of tert-butyl 3-[2-(4-cyanophenyl)imidazo[1,2-a]-pyridin-8-ylcarboxamido]propionate is stirred in 10 ml of a THF/dioxane mixture (1:1)with the addition of 2 ml of DMF in the presence of 0.14 g of KOH and 0.76 g of $K_2CO_3$ at room temperature for 2 h. After removal of the solvent, the residue is taken up in water and filtered. The customary working-up results in 3-[2-(4-cyanophenyl)-imidazo[1,2-a] pyridin-8-ylcarboxamido]propionic acid, m.p. 243°–248° (decomposition) (M+1:335).

The following are obtained analogously by hydrolysing the corresponding esters from Example 28:
3-[2-(4-cyanophenyl)imidazo[1,2-a]pyridin-7-ylcarboxamido]propionic acid;
2-[2-(4-cyanophenyl)imidazo[1,2-a]pyridin-7-ylcarboxamido]acetic acid;
2-[2-(4-cyanophenyl)imidazo[1,2-a]pyridin-7-yl-N-methylcarboxamido]acetic acid;
3-[2-(4-cyanophenyl)imidazo [1,2-a]pyridin-7-yl-N-methylcarboxamido]propionic acid;
2(S)-[2-(4-cyanophenyl)imidazo[1,2-a]pyridin-7-ylcarboxamido]succinic acid;
2(R)-[2-(4-cyanophenyl)imidazo[1,2-a]pyridin-7-ylcarboxamido]succinic acid;
1-[2-(4-cyanophenyl)imidazo[1,2-a]pyridin-7-ylcarbonyl]-piperidine-4-carboxylic acid;
1-[2-(4-cyanophenyl)imidazo[1,2-a]pyridin-7-ylcarbonyl]-4-(carboxymethoxy)piperidine;
1-[2-(4-cyanophenyl)imidazo [1,2-a]pyridin-7-ylcarbonyl]-4-(carboxymethyl)piperazine;
1-[2-(4-cyanophenyl)imidazo[1,2-a]pyridin-7-ylcarbonyl]-4-(2-carboxyethyl)piperazine;

Example 30

0.27 g of 3-[2-(4-cyanophenyl)imidazo[1,2-a]pyridin-8-ylcarboxamido]propionic acid is reacted with $H_2S$ gas in analogy to Example 3. 3-[2-(4-thiocarbamoylphenyl)imidazo[1,2-a]pyridin-8-ylcarboxamido]propionic acid, m.p. 267°–268° (decomposition) (M+1:369), is obtained.

The following are obtained analogously by reacting the compounds from Example 29 with $H_2S$:
3-[2-(4-thiocarbamoylphenyl)imidazo[1,2-a]pyridin-7-yl-carboxamido]propionic acid;
2-[2-(4-thiocarbamoylphenyl)imidazo[1,2-a]pyridin-7-yl-carboxamido]acetic acid;
2-[2-(4-thiocarbamoylphenyl)imidazo[1,2-a]pyridin-7-yl-N-methylcarboxamido]acetic acid;
3-[2-(4-thiocarbamoylphenyl)imidazo[1,2-a]pyridin-7-yl-N-methylcarboxamido]propionic acid;
2(S)-[2-(4-thiocarbamoylphenyl)imidazo[1,2-a]pyridin-7-ylcarboxamido]succinic acid;
2(R)-[2-(4-thiocarbamoylphenyl)imidazo[1,2-a]pyridin-7-ylcarboxamido]succinic acid;
1-[2-(4-thiocarbamoylphenyl)imidazo[1,2-a]pyridin-7-yl-carbonyl]piperidine-4-carboxylic acid;
1-[2-(4-thiocarbamoylphenyl)imidazo[1,2-a]pyridin-7-yl-carbonyl]-4-(carboxymethoxy)piperidine;
1-[2-(4-thiocarbamoylphenyl)imidazo[1,2-a]pyridin-7-yl-carbonyl]-4-(carboxymethyl)piperazine;
1-[2-(4-thiocarbamoylphenyl)imidazo[1,2-a]pyridin-7-yl-carbonyl]-4-(2-carboxyethyl)piperazine Example 31

0.2 g of 3-[2-(4-thiocarbamoylphenyl)imidazo[1,2-a]-pyridin-8-ylcarboxamido]propionic acid is reacted with methyl iodide in acetone in analogy to Example 4. 3-[2-(4-methyl sulfimidoylphenyl)imidazo[1,2-a]pyridin-7-ylcarboxamido] propionic acid is obtained.

The following are obtained analogously by reacting the compounds from Example 30 with methyl iodide:

3-[2-(4-methylsulfimidoylphenyl)imidazo[1,2-a]pyridin-7-ylcarboxamido]propionic acid;
2-[2-(4-methylsulfimidoylphenyl)imidazo[1,2-a]pyridin-7-ylcarboxamido]acetic acid;
2-[2-(4-methylsulfimidoylphenyl)imidazo[1,2-a]pyridin-7-yl-N-methylcarboxamido]acetic acid;
3-[2-(4-methylsulfimidoylphenyl)imidazo[1,2-a]pyridin-7-yl-N-methylcarboxamido]propionic acid;
2(S)-[2-(4-methylsulfimidoylphenyl)imidazo[1,2-a]pyridin-7-ylcarboxamido]succinic acid;
2(R)-[2-(4-methylsulfimidoylphenyl)imidazo[1,2-a]pyridin-7-ylcarboxamido]succinic acid;
1-[2-(4-methylsulfimidoylphenyl)imidazo[1,2-a]pyridin-7-ylcarbonyl]piperidine-4-carboxylic acid;
1-[2-(4-methylsulfimidoylphenyl)imidazo[1,2-a]pyridin-7-ylcarbonyl]-4-(carboxymethoxy)piperidine;
1-[2-(4-methylsulfimidoylphenyl)imidazo[1,2-a]pyridin-7-ylcarbonyl]-4-(carboxymethyl)piperazine;
1-[2-(4-methylsulfimidoylphenyl)imidazo[1,2-a]pyridin-7-ylcarbonyl]-4-(2-carboxyethyl)piperazine.

Example 32

4.0 g Of 4-(8-cyanoimidazo[1,2-a]pyridin-2-yl)benzoic acid and 2.14 g of ethyl 3-aminopropionate in 40 ml of DMF are stirred in the presence of 2.28 g of hydroxybenzotriazole, 3.0 g of N-methylmorpholine and 2.9 g of N-(3-dimethylaminopropyl)-N'-ethylcarbodiimide at room temperature for 4 h. After addition of 400 ml of water, the precipitate is filtered off with suction and washed successively with dilute bicarbonate solution and water. Methyl 3-[4-(8-cyanoimidazo[1,2-a]pyridin-2-yl)benzamido]propionate, m.p 201-204° is obtained.

Example 33

0.55 g of benzyl 3-[4-(8-cyanoimidazo[1,2-a]pyridin-2-yl)benzamido]propionate [obtainable by reacting 4-(8-cyanoimidazo[1,2-a]pyridin-2-yl)benzoic acid with benzyl 3-aminopropionate as in Example 32] is boiled in 30 ml of methanol with 0.27 g of hydroxylamine hydrochloride in the presence of 0.72 g of $K_2CO_3$ for 4 h. After cooling, the precipitate is filtered off with suction and washed successively with water and methanol. 3-[4-(8-cyanoimidazo[1,2-a]pyridin-2-yl)benzamido]propionic acid, m.p. 212°–215°, is obtained.

Example 34

The following amidino derivatives are obtained in analogy to Example 25 from the corresponding methylsulfimidoyl derivatives from Example 31:

3-[2-(4-amidinophenyl)imidazo[1,2-a]pyridin-7-ylcarboxamido]propionic acid;
2-[2-(4-amidinophenyl)imidazo[1,2-a]pyridin-7-ylcarboxamido]acetic acid;
2-[2-(4-amidinophenyl)imidazo [1,2-a]pyridin-7-yl-N-methylcarboxamido]acetic acid;
3-[2-(4 -amidinophenyl)imidazo[1,2-a]pyridin-7-yl-N-methylcarboxamido]propionic acid;
2(S)-[2-(4-amidinophenyl)imidazo[1,2-a]pyridin-7-ylcarboxamido]succinic acid;
2(R)-[2-(4-amidinophenyl)imidazo[1,2-a]pyridin-7-ylcarboxamido]succinic acid;
1-[2-(4-amidinophenyl)imidazo[1,2-a]pyridin-7-ylcarbonyl]piperidine-4-carboxylic acid;
1-[2-(4-amidinophenyl)imidazo[1,2-a]pyridin-7-ylcarbonyl]-4-(carboxymethoxy)piperidine;
1-[2-(4-amidinophenyl)imidazo[1,2-a]pyridin-7-ylcarbonyl]-4-(carboxymethyl)piperazine;
1-[2-(4-amidinophenyl)imidazo[1,2-a]pyridin-7-ylcarbonyl]-4-(2-carboxyethyl)piperazine.

The following examples relate to pharmaceutical compositions.

Example A: Vials

A solution of 100 g of an active substance of the formula I and 5 g of disodium hydrogen phosphate in 3 l of double-distilled water is adjusted to pH 6.5 with 2N hydrochloric acid, sterilized by filtration, dispensed into vials, lyophilized and sealed under sterile conditions. Each vial contains 5 mg of active substance.

Example B: Suppositories

A mixture of 20 g of an active substance of the formula I with 100 g of soya lecithin and 1400 g of cocoa butter is melted, poured into molds and left to cool. Each suppository contains 20 mg of active substance.

Example C: Solution

A solution is prepared from 1 g of an active substance of the formula I, 9.38 g of $NaH_2PO_4 \times 2H_2O$, 28.48 g of $Na_2HPO_4 \times 12H_2O$ and 0.1 g of benzalconium chloride in 940 ml of double-distilled water. The solution is adjusted to pH 6.8, made up to 1 l and sterilized by radiation. This solution can be used in the form of eye drops.

Example D: Ointment 500 mg of an active substance of the formula I are mixed with 99.5 g of petrolatum under aseptic conditions.

Example E: Tablets

A mixture of 1 kg of active substance of the formula I, 4 kg of lactose, 1.2 kg of potato starch, 0.2 kg of talc and 0.1 kg of magnesium stearate is compressed to tablets in a conventional manner so that each tablet contains 10 mg of active substance.

Example F: Coated Tablets

Tablets are compressed in analogy to Example E and are subsequently coated in a conventional manner with a coating composed of sucrose, potato starch, talc, tragacanth and colorant.

Example G: Capsules 2 kg of active substance of the formula I are used to fill hard gelatin capsules in a conventional manner so that each capsule contains 20 mg of the active substance.

Example H: Ampoules

A solution of 1 kg of active substance of the formula I in 60 l of double-distilled water is dispensed into ampoules, lyophilized under aseptic conditions and sealed in a sterile manner. Each ampoule contains 10 mg of active substance.

The preceding examples can be repeated with similar success by substituting the generically or specifically described reactants and/or operating conditions of this invention for those used in the preceding examples.

What is claimed is:

1. A compound of the formula I

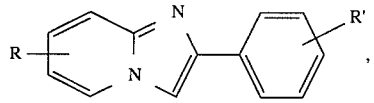

or a corresponding 5,6,7,8-tetrahydroimldazopyridine compound, in which

R is Q,

R' is COX,

Q is NH, C(=NH)—NH$_2$, CH$_2$—NH$_2$ or CH$_2$NHCO—alk—NH$_2$,

X is OH, AA, AA—AA'or

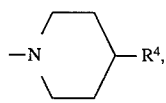

AA or AA' are each, independently of one another, an amino acid residue selected from the group consisting of β-Ala, Asp or Gly, A is alkyl with 1 to 6 C atoms, and —alk— is alkylene with 1 to 6 C atoms where any free amino or carboxyl groups can also be provided with protective groups known per se, and the physiologically acceptable salts and/or solvates thereof.

2. A compound of formula I of claim 1 which has a chiral center and its enantiomers or diastereomers.

3. A compound of the formula I according to claim 1 containing an amino, amidino or guanidino group which is protected by a conventional amino protective group.

4. A pharmaceutical composition comprising at least one compound of the formula I, according to claim 1, and/or one of its physiologically acceptable salts.

5. The method of controlling a disease which comprises administering a pharmaceutially effective amount of a compound of the formula I of claim 1, and/or one of its physiologically acceptable salts to a patient in need thereof, wherein the disease is controlled by action of the compound to inhibit the binding of fibrinogen, fibronectin or von Willebrand factor to the fibrinogen receptor of blood platelets (glycoprotein IIb/IIIa).

6. The method of claim 9, wherein the disease is thromboses, stroke, myocardial infarct, inflammation or arteriosclerosis and the compound inhibits the development of blood platelet thrombi.

7. The method of claim 9, wherein the disease is caused by tumors and the compound inhibits the metastasis of tumors.

8. The compound of claim 1, wherein X is an amino acid or dipeptide residue linked to the carbonyl group via an amide linkage.

* * * * *